(12) United States Patent  (10) Patent No.: US 6,748,266 B2
Bernabei  (45) Date of Patent: *Jun. 8, 2004

(54) METHOD AND APPARATUS FOR SKIN ABSORPTION ENHANCEMENT AND TRANSDERMAL DRUG DELIVERY

(75) Inventor: Gian Franco Bernabei, Florence (IT)

(73) Assignee: Mattioli Engineering Ltd., London (GB)

(*) Notice: Subject to any disclaimer, the term of this patent is extended or adjusted under 35 U.S.C. 154(b) by 0 days.

This patent is subject to a terminal disclaimer.

(21) Appl. No.: 10/201,644

(22) Filed: Jul. 24, 2002

(65) Prior Publication Data

US 2003/0014081 A1 Jan. 16, 2003

Related U.S. Application Data

(63) Continuation-in-part of application No. 10/074,234, filed on Feb. 14, 2002, which is a continuation-in-part of application No. 09/942,044, filed on Aug. 30, 2001, now Pat. No. 6,687,537, which is a continuation-in-part of application No. 09/922,927, filed on Aug. 7, 2001.
(60) Provisional application No. 60/281,808, filed on Apr. 6, 2001.

(51) Int. Cl.[7] .................................................. A61N 1/30
(52) U.S. Cl. ............................................. 604/20; 604/22
(58) Field of Search .................. 607/3, 149; 604/20–22, 604/500–501; 601/15, 17

(56) References Cited

U.S. PATENT DOCUMENTS

| 4,822,470 A | * | 4/1989 | Chang ........................ 435/450 |
| 4,887,594 A | * | 12/1989 | Siegel .......................... 601/71 |
| 4,907,601 A | | 3/1990 | Frick |
| 4,931,041 A | * | 6/1990 | Faeser ........................ 604/155 |
| 5,538,503 A | | 7/1996 | Henley |
| 5,658,247 A | | 8/1997 | Henley |
| 5,667,487 A | | 9/1997 | Henley |
| 5,688,233 A | * | 11/1997 | Hofmann et al. ............. 604/20 |
| 5,830,177 A | * | 11/1998 | Li et al. ........................ 604/22 |
| 5,983,131 A | * | 11/1999 | Weaver et al. ................ 604/20 |
| 6,009,345 A | | 12/1999 | Hofmann |
| 6,302,874 B1 | * | 10/2001 | Zhang et al. ............... 604/522 |
| 6,424,862 B1 | | 7/2002 | Brown, III et al. |
| 6,535,761 B2 | * | 3/2003 | Bernabei ........................ 607/3 |

FOREIGN PATENT DOCUMENTS

| EP | 0 625 360 A1 | 11/1994 |
| GB | 1007143 | 7/1967 |
| WO | WO 00/02620 A1 | 1/2000 |
| WO | WO 02/49717 | 6/2002 |

* cited by examiner

Primary Examiner—Mark Bockelman
(74) Attorney, Agent, or Firm—Foley & Lardner LLP

(57) ABSTRACT

Application of electrical pulses is made in a controlled manner, in order to increase the absorption of substances applied previously on the skin. Optionally, mechanical vibrations may also be provided to the skin to increase the absorption effect. The electrical pulses are provided to the skin by way of an array of electrodes disposed on a vibrating head plate, and the mechanical vibrations are provided to the skin by way of the vibrating head plate being made to vibrate (if that option is utilized). Preferably, the electrical and mechanical vibrations are at the same frequency and phase with respect to each other, in order to increase the absorption effect. Also, at the same time the electrical pulses are provided to the skin, a syringe containing a skin enhancement substance or a drug is actuated so as to move a particular amount of the substance from the skin, whereby the substance is passed through a tube and then into a groove surrounding a central electrode of the array of electrodes disposed on the plate. The substance is absorbed within the skin as a result.

14 Claims, 12 Drawing Sheets

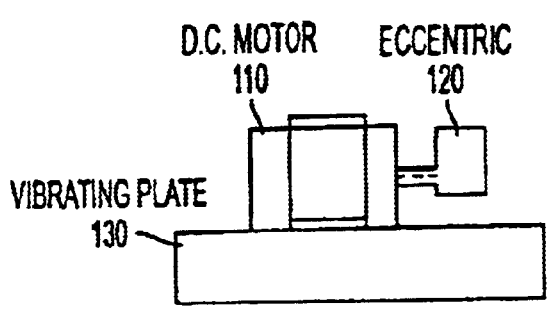
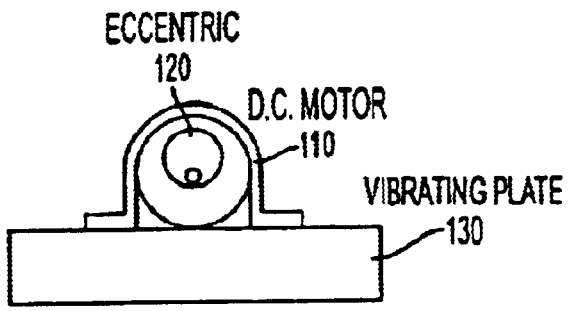
FIG. 1A  FIG. 1B
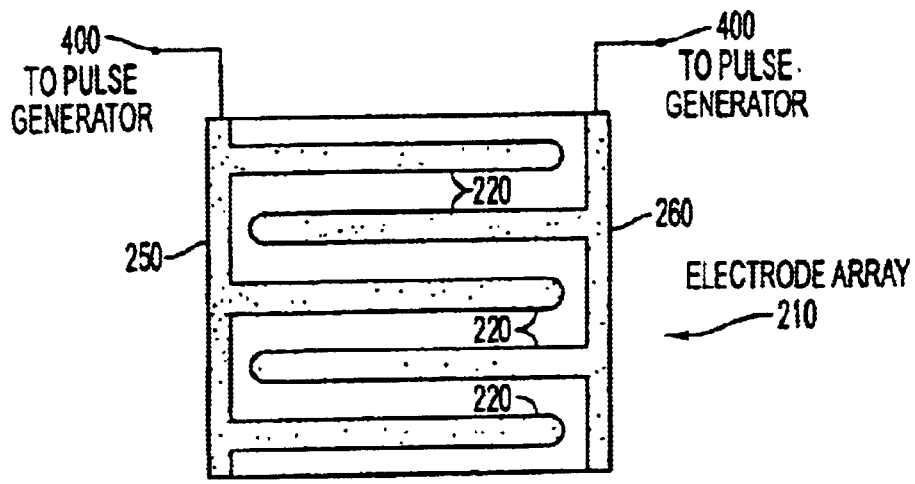
FIG. 2A
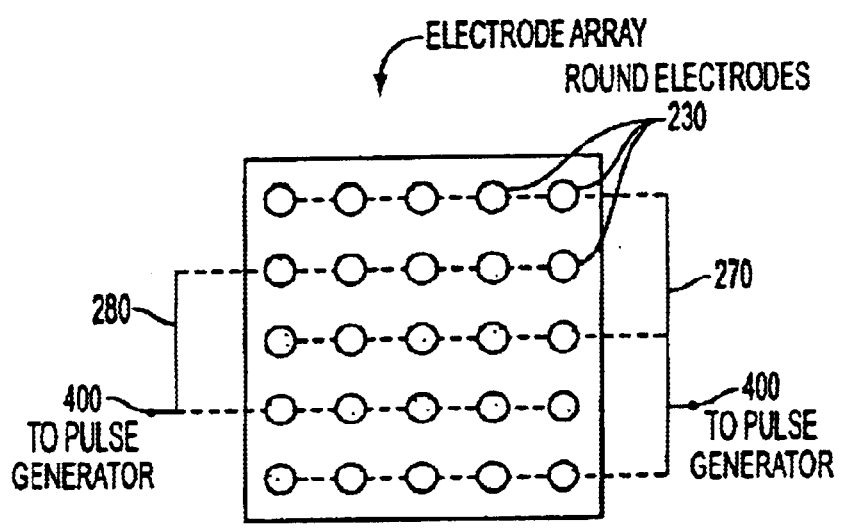
FIG. 2B

METHOD AND APPARATUS FOR SKIN ABSORPTION ENHANCEMENT AND TRANSDERMAL DRUG DELIVERY

CROSS-REFERENCE TO RELATED PATENT APPLICATIONS

This application claims priority to U.S. Provisional Application No. 60/281,808, filed Apr. 6, 2001, and whereby this application is a continuation-in-part of U.S. patent application Ser. No. 10/074,234, filed Feb. 14, 2002 pending, which in turn is a continuation-in-part of U.S. patent application Ser. No. 09/942,044, filed Aug. 30, 2001 now U.S. Pat. No. 6,687,537, which in turn is a continuation-in-part of U.S. patent application Ser. No. 09/922,927, filed Aug. 7, 2001 now U.S. Pat. No. 6,535,761, each of which is incorporated in its entirety herein by reference.

BACKGROUND OF THE INVENTION

1. Field of the Invention

The invention relates to application of electrical pulses and mechanical vibrations to the skin in a controlled manner, in order to increase the absorption of a substance that is applied at the same time to the skin by way of a syringe.

2. Description of the Related Art

It is known that an electrical pulse applied to the skin is useful in order to increase the absorption of a substance previously applied to the skin, whereby this technique is known as electroporation. Such a substance to be applied to the skin may be a liquid, a gel, a lotion, or a cream, for example.

It is desired to provide an apparatus and a method to increase the absorption of a substance to be applied to the skin, in order to obtain an increased (e.g., moisturizing) affect of the substance applied to the skin.

SUMMARY OF THE INVENTION

The present invention is directed to an apparatus and a method for enhancing the absorption of a substance to be applied on the skin.

To accomplish this, the present invention uses a sequence of electrical pulses (between 20 and 200V peak to peak, preferably, and between 50 and 15,000 Hz preferably) provided to electrodes that are placed in contact with the skin. There is also provided a corresponding surface vibration to the skin, by application of a mechanical vibration to the skin. The mechanical vibration is preferably of the same frequency and phase as the electrical pulses applied to the skin. The mechanical vibration is provided by way of a vibrating plate that also contains the electrodes (which provide the electrical stimulus to the skin at the same time the mechanical vibration is provided to the skin). In an alternative configuration, only electrical pulses are provided to the skin, whereby mechanical vibrations are not utilized.

The substance to be absorbed by the skin is applied to the skin by way of a syringe, which outputs the substance by way of a tube that is connected to an output of the syringe at one end of the tube and where the other end of the tube is disposed adjacent to a groove (or trough) surrounding a central electrode of an array of electrodes. Such a substance that is provided to the skin may be a cream, liquid or gel (for example, collagen, or cocoa butter, or suntan oil, or other types of skin enhancement lotions), or a drug to be administered into the skin.

The method according to an embodiment of the invention includes:

1) An apparatus which includes the following elements to perform the following treatment:
   a) a probe having an array of electrodes on a head portion of the probe, with a central electrode disposed at a central location on the head portion and with a plurality of circumferential electrodes disposed around the central electrode.
   b) a pulse generator connected to the array of electrodes.
   c) a vibrator which vibrates the head portion of the probe at a same time the electrical pulses are provided to the array of electrodes on the head portion.
   d) a syringe that provides a substance to the skin under control of a motor that outputs the substance from the syringe in a controlled manner, whereby the substance is provided to a groove or trough that surrounds the central electrode.

During operation, as electrical pulses are provided to the skin by way of the electrodes on the head of the probe, and, at the same time, mechanical vibrations are provided to the skin by way of the vibrating head portion, the substance disposed within the trough surrounding the central electrode is absorbed within the skin due to the skin pores opening up as a result of the electrical pulses and mechanical vibrations being applied to the skin. Alternatively, only electrical pulses are provided to the skin, which does not provide as good a skin absorption effect as using both electrical pulses and mechanical vibrations.

BRIEF DESCRIPTION OF THE DRAWINGS

The foregoing advantages and features of the invention will become apparent upon reference to the following detailed description and the accompanying drawings, of which:

FIG. 1A is a side view of a vibration mechanism that is disposed within an apparatus according to the present invention;

FIG. 1B is a front view of the vibration mechanism of FIG. 1A;

FIG. 2A shows an array of electrodes provided on an outer surface of the vibration plate that faces the skin, according to a first embodiment of the invention;

FIG. 2B shows an array of electrodes provided on an outer surface of the vibration plate that faces the skin, according to a second embodiment of the invention;

DETAILED DESCRIPTION OF THE PREFERRED EMBODIMENTS

Figure 2C:
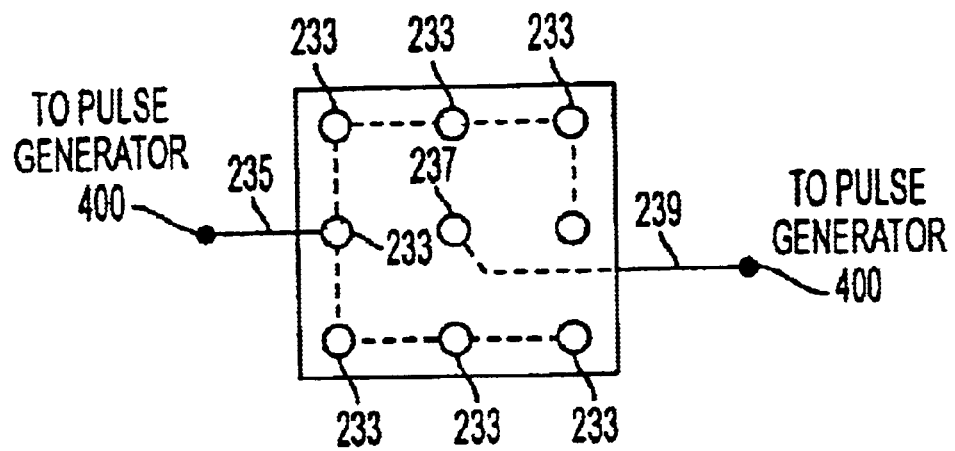
FIG. 2C shows an array of electrodes provided on an outer surface of the vibration plate that faces the skin, according to a third embodiment of the invention.

Preferred embodiments of the invention will be described in detail below, with reference to the accompanying drawings.

Based on experimental tests on the skin, it has been found by the inventor that after one or more pulses are applied between two points on the skin, transpiration (or absorption) in the area between the two points on the skin increases. The pulses that give optimal results are exponential pulses that are generated by a charged capacitor that is discharged on at least two separate points on the skin.

These experimental results have been utilized by the inventor in order to develop an apparatus and method that maintains the transpiration of the skin at a high level, so that the skin can readily absorb a gel, liquid, lotion, cream, or drug that is applied to the skin. The drug may be used to treat skin melanoma and/or cancerous tumors located just below the skin surface, for example.

The apparatus according to an embodiment of the present invention applies a sequence of pulses over an area or skin, by using an array of electrodes that are placed in contact with the skin. The array of electrodes are provided on a vibrating plate at the head of a probe, such as a hand-held probe 500 as shown in FIG. 5. The array of electrodes may be a configured as shown in FIG. 2A in a first embodiment, whereby odd rows of electrodes are electrically connected to each other, and thereby to a first output of a pulse generator 400 (see also FIG. 4) via a first electrical connection. The even rows of electrodes are electrically connected to each other, and also to a second output of the pulse generator 400 via a second electrical connection. The array of electrodes on the vibrating plate may alternatively be configured as shown in FIG. 2B in a second embodiment, whereby odd rows of round electrodes are electrically connected to each other, and thereby to the first output of the pulse generator 400 via a first electrical connection. The even rows of round electrodes are electrically connected to each other, and thereby to the second output of the pulse generator 400 via a second electrical connection.

The increase of the transpiration of the skin that is obtained by way of the present invention has the effect of increasing the absorption of liquids, creams, lotions, gels, or skin treatment drugs (or other kinds of drugs) that have been previously provided on the skin in the area between where the electrodes are applied to the skin.

The electrical pulses that are applied on the skin in order to enhance the transpiration of the skin are pulses obtained by a discharge of a capacitor on the skin. A square-wave pulse input to a primary winding of the transformer 410 of FIG. 4, with an output of the secondary winding of the transformer 410 being coupled to the skin by way of the electrodes, provides the same effect as a discharging capacitor. The exponential pulses are generated during the rising edge and falling edge of each square-wave input pulse that is input to the transformer 410 from a square-wave pulse generator, and have opposite sign (positive exponential pulse due to the rising edge of a square-wave input pulse, negative exponential pulse due to the falling edge of the same square-wave input pulse). With the use of such a pulse generator 400 as shown in FIG. 4, it is possible to apply a burst of separate pulses (e.g., 500 to 1500 per second) to the skin, with adjacent pulses being of opposite polarity and which provides a transpiration effect better than just providing one pulse or many pulses of the same polarity to the skin.

Figure 4:
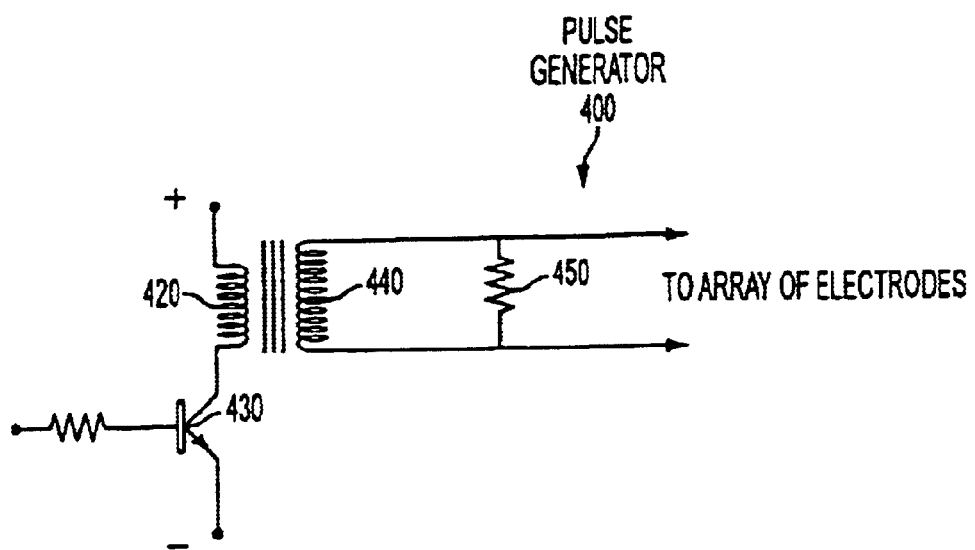
FIG. 4 shows an electrical diagram of a pulse generator that provides electrical pulses to an array of electrodes disposed on a vibrating plate provided at a head-end of the probe, according to one possible configuration of an apparatus according to the invention.
Figure 4A:
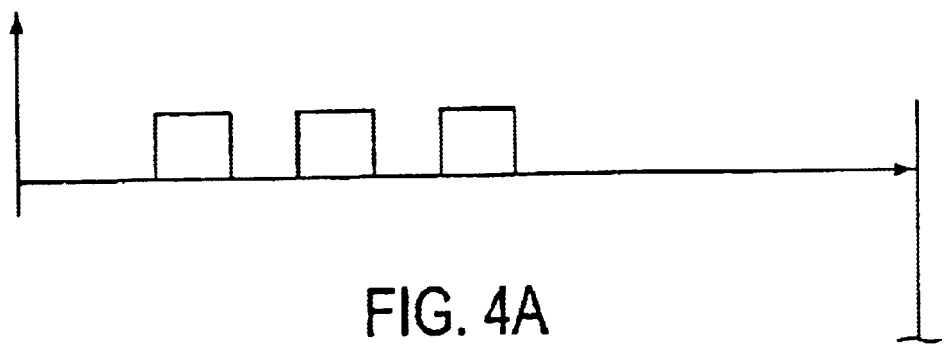
FIG. 4A shows a train of square-wave pulses that are input to the pulse generator of FIG. 4.
Figure 4B:
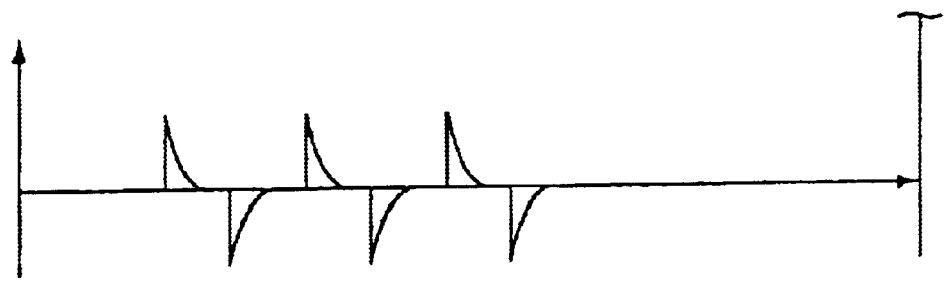
FIG. 4B shows a train of exponential pulses that are output from the pulse generator of FIG. 4.
Figure 5:
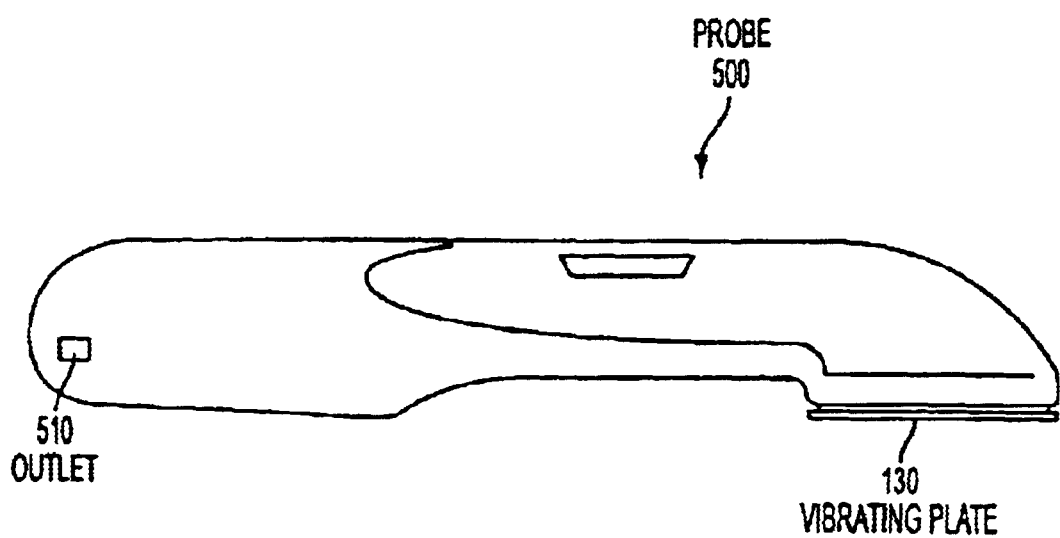
FIG. 5 shows one configuration of a hand-held probe that is used to provide both electrical and mechanical stimulation to the skin, according to one or more embodiments of the invention.

Switching transistor 430 provides square-wave pulses as shown in FIG. 4A to the primary winding of the transformer 410, as shown in FIG. 4. The pulses generated by the pulse generator 400 of FIG. 4, when the load is a pure resistance (or inductive or other type of reactive load), is a sequence of exponential decay pulses of opposite symmetrical polarities, as shown in FIG. 4B. Such a circuit that includes the pulse generator 400 provides an excellent coupling to the impedance of the skin. Moreover, the inductance of the transformer 410 together with the capacitance of the skin generates a resonant circuit, which is desirable to achieve an opening of the skin pores or membranes.

The voltage waveform is conveniently modified when applied to the skin due to the fact that the electrical equivalent circuit of the skin is a resistance and a capacitance in parallel. The resulting voltage waveform has a longer rise time (due to the RC time constant), and is dependent upon the capacitance of the skin, while maintaining the same peak current and the same exponential decay waveform.

Such a circuit according to the first embodiment gives an advantage in comparison to traditional pulse generators that deliver pulses of a predefined value and shape of tension or current. By way of the present invention according to the first embodiment, it is possible to deliver higher energy value per pulse, and also at the same time avoid possible damage to the skin that would occur if high current amounts were applied to the skin. The circuit utilized in the first embodiment self adjusts the value of the current, tension and waveform shape. In particular, the impedance of the skin decreases after the first pulse is applied to the skin. In this way, the voltage of the first pulse is higher than subsequent pulses, since the impedance of the skin is higher at the time the first pulse is applied to the skin. The voltage of the second and following pulses applied to the skin decreases with the decreasing of the impedance of the skin, while maintaining the peak current at the same or almost the same value.

Typical values of current and tension are provided herein. Case 1: load impedance of 10 kohm, peak voltage of 100 V, peak current of 10 milliamperes, pulse width of 220 microseconds. Case 2: load impedance of 1 kohm, peak voltage of 10 V, peak current of 10 milliamperes, pulse width of 220 microseconds. The pulses are preferably delivered in bursts, where the burst rate is the same as the mechanical vibration rate. A typical value of the burst rate (and mechanical rate) is between 40 Hz and 100 Hz.

Normally, when a square wave is applied to the skin, due to the capacitive effect of the skin, it is possible to obtain about a three microsecond time constant exponential decay current. This is what happens when a square wave voltage is applied to a circuit that corresponds to a resistor in parallel with a capacitor.

With such a circuit, only the peak current is enhanced, charging to a maximum allowable voltage the skin capacitance by applying an electrical energy equal to the magnetic energy of the transformer 410. This effect most likely provides for the opening of the cell membranes or pores of the skin (to achieve the transpiration effect) only during the time when each pulse is applied to the skin.

The effect of applying the probe to the skin is that the skin vibrates due to the electrical pulses applied by way of the array of electrodes. The electrical pulses are preferably applied at a fixed frequency between 200 and 10,000 Hz (optimally at a frequency value between 2,500 to 3,000 Hz), and are grouped in a burst. The ON time of each burst is a fixed value between 5 to 50 milliseconds, and the OFF time between two consecutive bursts is a fixed value between 5 to 50 milliseconds (the preferred burst ON time is 10 milliseconds and the preferred OFF time between consecutive bursts is 10 milliseconds).

As described above, the electrical pulses applied to the skin by way of the electrodes are preferably exponential pulses with peak-to-peak voltage of 160 V at a fixed frequency between 2,500 to 3,000 Hz. One way of providing such electrical pulses is by an electrical structure that corresponds to a pulse generator 400 as shown in FIG. 4, in which a transformer 410 is used as an element of the pulse generator 400.

The transformer 410, as well as the other elements of the pulse generator 400, are preferably housed within the probe 500 of FIG. 5.

Referring back to FIG. 4, the primary winding 420 of the transformer 410 is driven by a transistor 430 that is switched on and off, and the secondary winding 440 of the transformer 410 is directly applied to the array of electrodes (see FIG. 1A or 1B) with an electrical resistance 450 provided therebetween. The electrical resistance 450 may be 200 Kohm or some value in that range (e.g., 100 Kohm to 500 Kohm), and is provided in order to avoid high voltages when the array of electrodes are not applied to the skin, so that in that case it operates as an open circuit. In such a situation, the peak-to-peak voltage is 400 V or thereabouts.

Along with the electrical pulses applied to the skin, a mechanical vibration is also provided to the skin in the first embodiment in order to increase the absorption of a substance that is applied on the skin.

The absorption effect is enhanced by the simultaneous increase of transpiration, whereby the absorption effect is greatest when the mechanical vibration is synchronized in phase and in frequency with the electric pulse application. Thus, in the example discussed above, while the electrical burst of pulses (at 2,200 Hz) are provided to the skin at a burst ON/OFF frequency, e.g., 50 Hz, by way of an electrode array, the skin is also mechanically vibrated at the same frequency, e.g., 50 Hz, by way of the vibrating plate. The mechanical vibration and the electrical burst application are also preferably provided in phase with respect to each other, in order to increase the skin absorption effect. There are several well known ways to achieve this frequency and phase synchronization. In the preferred embodiments described herein, an optical sensor (not shown) detects the movement of the eccentric of a motor that is used to provide the mechanical vibrations (see FIGS. 1A and 1B, for example), and gates the burst of electrical pulses based on the detected movement.

Thus, in the example discussed above, while the burst of electrical pulses are provided to the skin by way of the electrode array, the skin is also mechanically vibrated at the same frequency by way of the vibrating plate. The mechanical vibration and electrical pulse application is also preferably provided in phase with respect to each other, in order to increase the skin absorption effect.

Moreover, the absorption effect is further enhanced when the mechanical vibration is applied orthogonal to the surface of the skin. While Applicant does not intend to be tied down to any particular theory of operation, one possible explanation of the physical phenomena of one or more embodiments of the present invention is that, while the electrical pulses "stretch" the skin, thus increasing periodically the diameter of the pores of the skin, at the same time the mechanical vibration "pumps" the substances (gel, liquid or cream) inside the skin (through the opened pores). The mechanical and electrical synchronization achieves the effect that the "pumping" action (due to the mechanical stimulation of the skin) takes place at the same instant in time that the pores are at their maximum "open" diameter (due to the electrical stimulation of the skin).

The apparatus according to a first embodiment the present invention includes a probe having two main parts:

A) a handle containing a power source (e.g., batteries) and a pulse generator; and B) a vibrating head containing components for generating the vibration and also containing an array of electrodes.

The vibrating head, in a preferred configuration, includes a D.C. electrical motor for generating vibrations to the skin. FIGS. 1A and 1B show two different views of the D.C. electrical motor 110, the rotating shaft of the D.C. electrical motor 110 is an eccentric 120 to thereby provide eccentric motion. The eccentric motion, during rotation of the D.C. electrical motor 110, generates a vibration onto the vibrating plate 130 (that is directly coupled to the D.C. electrical motor 110) that is at the same frequency of the rotation of the D.C. electrical motor 110 (e.g., 50 Hz or 60 Hz or some other desired frequency). Other ways of causing vibrations in synchronization with the providing of electrical pulses to a patient may be contemplated while remaining within the scope of the invention.

As explained earlier, FIG. 4 shows circuitry for providing electrical pulses to the array of electrodes shown in FIGS. 2A and 2B. The circuitry of FIG. 4 corresponds to a pulse generator 400, and is preferably disposed within the housing of the probe 500 of FIG. 5. The electrical pulses generated by the pulse generator 400, when those pulses are provided to the skin, preferably are exponential pulses with peak-to-peak voltage of 160 V at a frequency of between 2,500 Hz to 3,000 Hz. Of course, other peak-to-peak voltage values (e.g., 100 V to 200 V) and operating frequencies (50 Hz to 15,000 Hz) may be employed, while remaining within the scope of the invention as described herein. Alternatively, sawtooth or sinusoidal pulses may be provided to the electrodes, but exponential pulses appear to provide better skin transpiration results.

FIGS. 1A and 1B show the vibrating plate 130 that is physically coupled to the D.C. electrical motor 110. The vibrating plate 130 preferably is 50×50 mm in size (other sizes are possible while remaining within the scope of the invention), where parallel metallic stripes are deposited on it as shown in FIG. 2A, in order form the array of electrodes. The vibrating plate 130 is caused to vibrate at the same phase and frequency as the electrical pulses provided to the skin by way of the array of electrodes (disposed on the vibrating plate), in order to enhance the skin absorption effect.

As shown in FIG. 2A, which shows a first embodiment of an electrode array 210 that is provided on a skin-side surface of the vibrating plate 130, five parallel metallic stripes 220 are provided, each preferably of a size of 50 mm×4 mm. Each of the five electrodes 220 are preferably 6 mm apart from adjacently-positioned electrodes. The electrodes 220 are alternately electrically connected (e.g., the first, third and fifth row are electrically connected to each other by way of electrical line 250; and the second and fourth rows are electrically connected to each other by way of electrical line 260). Other electrode array configurations are possible while remaining within the scope of the invention, such having a number of electrodes greater than two, such as having seven or eight electrodes.

FIG. 2B shows a second embodiment of an electrode array that is provided on a skin-side surface of a vibration plate. In FIG. 2B, there are provided 25 round electrodes 230 each of 4 mm diameter, each separated at least 6 mm from adjacently-positioned round electrodes. The round electrodes 230 are alternately electrically connected to each other (e.g., the electrodes on the first, third and fifth rows are electrically connected to each other by way of electrical line 270; and the electrodes on the second and fourth rows are electrically connected to each other by way of electrical line 280). The spacing between the electrodes 230 shown in FIG. 2B may vary between 1 to 20 mm and the size of each of the electrodes 230 may vary between 1 to 20 mm in diameter.

FIG. 2C shows an array of electrodes provided on an outer surface of the vibration plate that faces the skin, according to the third embodiment of the invention. In FIG. 2C, there are provided electrodes 233 that are disposed on the periphery of the vibration plate, which are electrically coupled to each other, and which are electrically coupled to a first output of the pulse generator 400 by way of a first electrical connection 235. In FIG. 2C, there is also provided a centrally-positioned electrode 237, which is not electrically coupled to any other of the electrodes, and which is electrically coupled to a second output of the pulse generator 400 by way of a second electrical connection 239.

Figure 3:
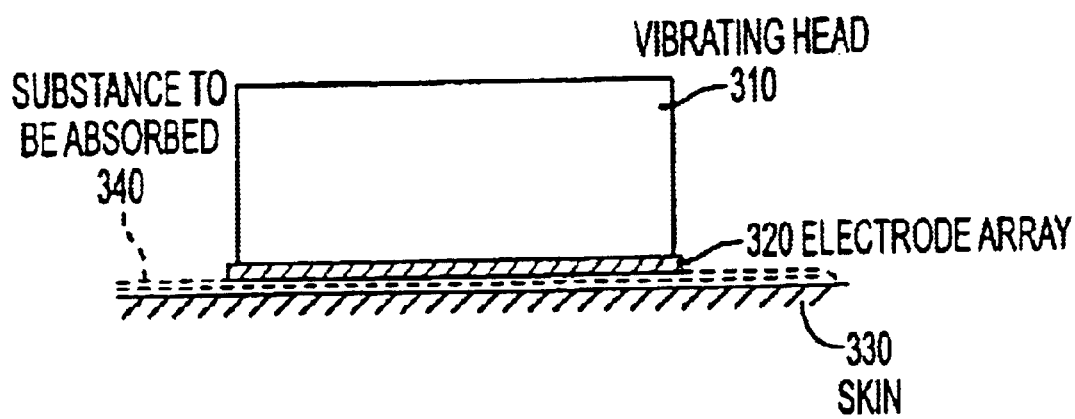
FIG. 3 shows a side view of a head of a probe that is used to provide both electrical and mechanical stimulation to the skin, in order to have a substance previously applied to the skin to be absorbed better, according to the invention.

FIG. 3 shows a side view of a vibrating head 310 of a probe that is used to provide both electrical and mechanical stimulation to the skin according to an embodiment of the present invention, in order to have a substance previously applied to the skin be absorbed better. As shown in FIG. 3, the vibrating head 310 includes the array of electrodes 320 provided on a skin-side surface thereof. The array of electrodes 320 may be provided in a manner such as shown in either FIG. 2A or 2B, for example. Between the array of electrodes 320 and the skin 330 there is provided a substance 340 to be absorbed, whereby the substance 340 has been previously applied to the skin 330 (e.g., applied to the skin between 30 seconds to 2 minutes before the probe is to be applied to the skin 330). Application of mechanical vibrations and electrical pulses enhances the absorption of the substance 340 into the skin 330.

FIG. 5 shows one configuration of a hand-held probe 500 that may be used to provide both electrical and mechanical stimulation to the skin, according to one or more embodiments of the invention. The probe 500 is configured to be readily held by one hand of a user. A bottom portion of the probe 500, at which a user's hand is gripped thereon to thereby hold the probe 500, may include an outlet 510 for coupling an electrical cable to an electrical outlet (e.g., wall outlet), so as to provide A.C. voltage to the probe 500 in that manner. Alternatively, battery power may be used, by way of batteries (not shown) disposed within the housing of the probe 500. Battery power may be utilized when A.C. power is not readily available. Also, the pulse generator 400 of FIG. 4 is preferably housed at the handle portion of the probe 500.

The head portion of the probe 500 is where the vibrating plate 130 (see FIG. 1A or 1B) is provided, and also where the D.C. electrical motor 110 (see also FIG. 1A or 1B) that provides the mechanical vibrations to the vibrating plate 130 is preferably provided housed within. The array of electrodes (see FIG. 2A or 2B) are provided on an outer surface of the vibrating plate 130, thereby facing the skin of a user to be treated with the probe 500.

A typical application time of the probe to the skin may be on the order to 10 s of seconds up to several minutes.

Figure 6:
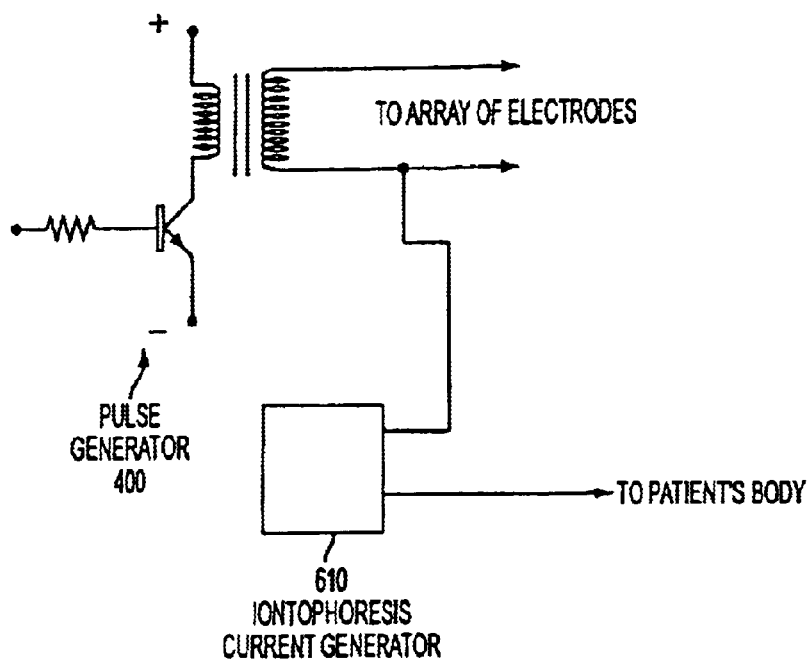
FIG. 6 shows a current generator connection according to a fourth embodiment of the invention.

In a fourth embodiment, as shown in FIG. 6, the output of the pulse generator 400 (see also FIG. 4) is connected to a D.C. current generator 610, which induces a iontophoresis effect in addition to the previously described skin absorption/transpiration effects. The iontophoresis effect is well known to those skilled in the art, and several iontophoresis electrical generators are currently available in the market, either D.C. or D.C. pulsed. A D.C. current output by the D.C. current generator 610 is applied between the electrodes of the probe and a ground plate that is connected with the patient's body. Depending on the substance to be absorbed into the patient's skin, the patient ground plate connection is coupled to either the positive or the negative of the D.C. current generator 610, in a manner known to those skilled in the art. Instead of using continuous D.C. current, there can alternatively be provided D.C. current pulses that have the same average current value as the continuous D.C. current case, and which have a duty cycle between 5 and 50% and a frequency between 10 and 5000 Hz. In such a case, the peak current of the D.C. current pulses is higher during the pulsed (ON) times.

Figure 7:
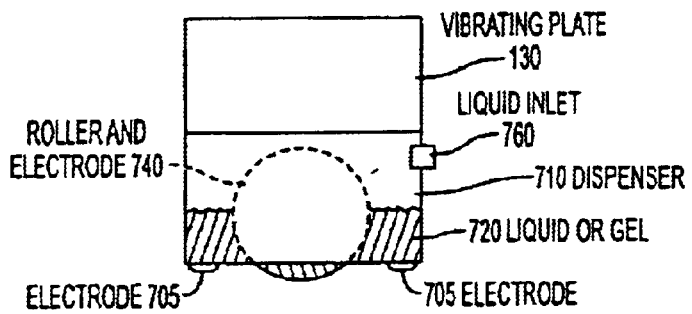
FIG. 7 shows elements provided at the head portion of a probe, according to a fifth embodiment of the invention.
Figure 8:
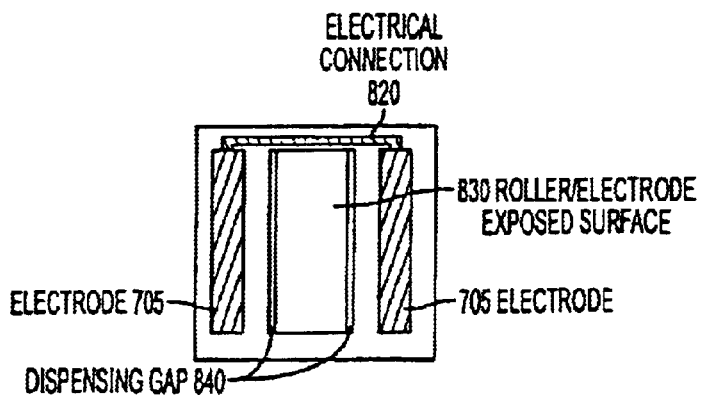
FIG. 8 shows a front view of the head portion of the probe according to the fifth embodiment of the invention.

In a fifth embodiment, as shown in FIGS. 7 and 8, a dispenser or chamber 710, which is configured to hold liquid or cream or gel 720, is integrated in the vibrating head of the probe. The dispenser or chamber 710 is provided between an array of electrodes 705 and the vibrating plate 130. The burst of electrical pulses are applied by way of a conductive roller 740 that dispenses the liquid, and by the array of electrodes 705. A D.C. current as in the third embodiment can also be added between the array of electrodes 705 and the patient's body, to induce a iontophoresis effect as well. While the vibrating head is moved on the patient's skin, the roller 740 delivers the liquid or cream or gel 720 to the patient's skin.

The chamber 710 in which the roller 740 is disposed in the vibrating head can be filled with a liquid, cream or gel substance 720 by way of a removable cap (not shown). In particular, the cap is removed (e.g., screwed off of the head of the probe), and then a user fills the chamber 710, through the liquid inlet 760, with the substance 720 to be provided to the patient's skin. The user then closes the cap (e.g., screws it back onto the liquid inlet 760) to thereby keep the substance 720 within the chamber 710 of the probe until it is ready to be applied to the patient's skin by way of the roller 740.

FIG. 8 shows a front view of the electrodes 705, which are shown as two stripe electrodes that are electrically connected to each other by way of electrical connection 820. Of course, other types of electrode arrays, such as those shown in FIGS. 2A and 2B, can alternatively be used in this fifth embodiment. The exposed surface 830 of the roller 740 that applies the substance to the patient's skin, is shown in FIG. 8. Dispensing gaps 840 are also shown in FIG. 8, whereby these gaps 840 allow the liquid, cream or gel substance 720 in the chamber 710 to gradually come out of the chamber 710 and thereby be applied to the patient's skin by way of the roller 740.

In a sixth embodiment of the invention, an apparatus for enhancing absorption of the skin includes an array of electrodes, and a pulse generator that is electrically coupled to the array of electrodes. The disposition of the array of electrodes may be any of the dispositions shown in FIGS. 2A–2C, for example. In a preferred implementation of the sixth embodiment, electrical pulses outputted by the pulse generator 400 to the array of electrodes are a sequence of exponential pulses, such as the pulse train shown in FIG. 4B. The exponential electrical pulses are applied to the skin by way of the array of electrodes and are generated by the secondary winding of a high voltage transformer with the primary winding driven by a square wave voltage, as seen by FIGS. 4, 4A and 4B.

In the sixth embodiment, unlike the previous embodiments, a vibrating head is not utilized, but rather skin absorption enhancement is obtained just by the providing of the electrical pulses to the skin by way of the array of electrodes. The array of electrodes according to the sixth embodiment are provided on a plate at the head of the probe, whereby the head and the plate do not vibrate. Thus, in the sixth embodiment, the structure as shown in FIGS. 1A and 1B would not be utilized, but rather just a plate for holding the electrodes in place at the head of the probe would be needed.

In a seventh embodiment, a vibrating head is utilized, as in the first through fifth embodiments, but where the vibrating head is capable of being turned on or off, by way of a control (e.g., switch) provided on the probe. The control can readily be manipulated by an operator of the probe, in order to treat a patient.

Figure 9:
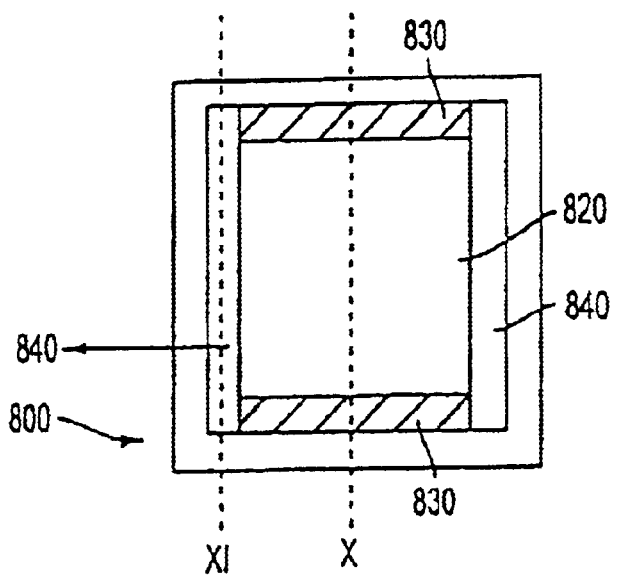
FIG. 9 shows a front view of the head portion of the probe according to an eighth embodiment of the invention.
Figure 10:
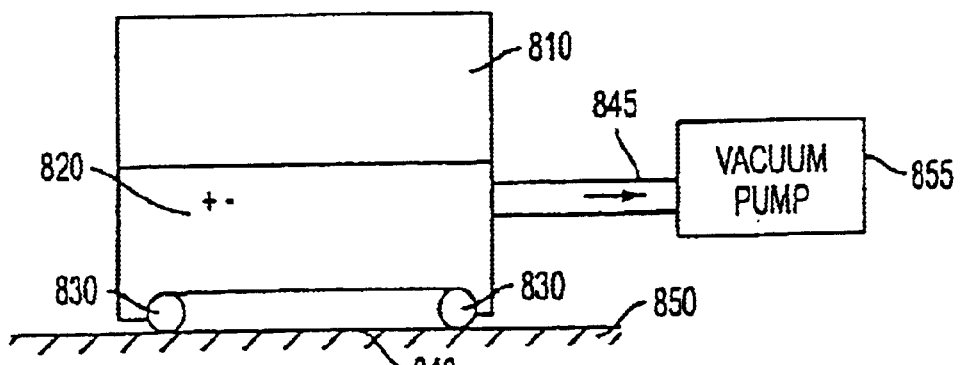
FIG. 10 shows a first section view of the head portion of the probe according to the eighth embodiment of the invention, whereby suction is not being applied to the skin.
Figure 11:
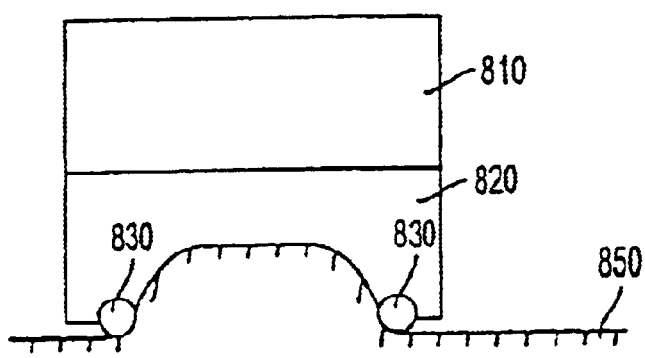
FIG. 11 shows a second section view of the head portion of the probe according to the eighth embodiment of the invention, in which suction is being applied to the skin.

An eighth embodiment of the invention is described below, with reference to FIGS. 9–11. FIG. 9 shows a front view of a head 800 of a probe, whereby that view shows the portion of the probe that is applied to the skin of a patient. FIG. 10 shows a section view taken along an axis of one belt, and FIG. 11 shows a section view taken at the middle of the head of the probe.

The eighth embodiment provides for a fairly even absorption under the skin of a substance previously applied to the skin, such as collagen previously applied to the skin. In the eighth embodiment, a head 800 of a probe to be applied to the skin includes a vibrating plate 810, a vacuum chamber 820, rollers 830, and belts 840 disposed around the rollers 830. The rollers 830 are conductive rollers, whereby the rollers 830 are electrically coupled to electrodes (see FIGS. 2A through 2C, for example) provided on the vibrating plate 810. As in the other embodiments, a pulse generator (see FIG. 4, for example) is electrically coupled to the electrodes on the vibrating plate 810, in order to provide electrical pulses to the patient's skin (by way of the conductive rollers).

In the eighth embodiment, the rollers 830 are separated from each other by around 40 mm. Of course, other separation distances are possible, while remaining within the scope of the invention (e.g., 20 mm to 80 mm separation). The rollers 830 are disposed at one end of the vacuum chamber 820, whereby the vacuum chamber 820 includes an opening that is coupled to a pipe 845 that is in turn coupled to a vacuum pump 855.

When the vacuum pump 855 is operated, the vacuum chamber 820 generates a suction effect on the skin 850, thereby enabling a stronger contact between the rollers 830 and the skin 850, and thereby generating an additional massaging effect to the skin 850, in addition to the vibrations generated by the vibrating plate 810. On opposite ends of the rollers 830 are the belts 840, which are preferably rubber belts. The belts 840 are used in order to avoid direct friction between the skin 850 and the body of the vacuum chamber 820.

The eighth embodiment provides good skin absorption results and decreases the appearance of cellulite on the skin after application of a substance for reducing cellulite is applied to the skin. Such a substance for reducing cellulite that can be applied to the skin may be jarulon acid, for example. Such a substance could also be previously spread on the skin and absorbed by the skin utilizing one of the previously-described embodiments.

Also, while the eighth embodiment has been described as having a vibrating plate, as in the first through fifth embodiments, a non-vibrating plate as in the sixth and seventh embodiments (when the vibrating plate is turned off) may be utilized in an alternative configuration. In that case, the plate disposed above the vacuum chamber is non-vibrating, and contains electrodes disposed therein.

A ninth embodiment of the invention will be described in detail hereinbelow with reference to FIGS. 12–14. The ninth embodiment includes a motor 1, a screw 2, a slide 3, a frame 4, a piston 5, a syringe 6, a pipe (or tubing) 7, a central electrode 8, and circumferential electrodes 9 (that are disposed outside of the central electrode 8) on a head 10. The head 10 is a head portion of a probe, such a probe shown in FIG. 5 in the previous embodiments (except for the fifth embodiment, whereby the substance is disposed within a chamber within the head that is adjacent to the electrode plate, and thus a syringe would not be needed in that case), for example.

Figure 12:
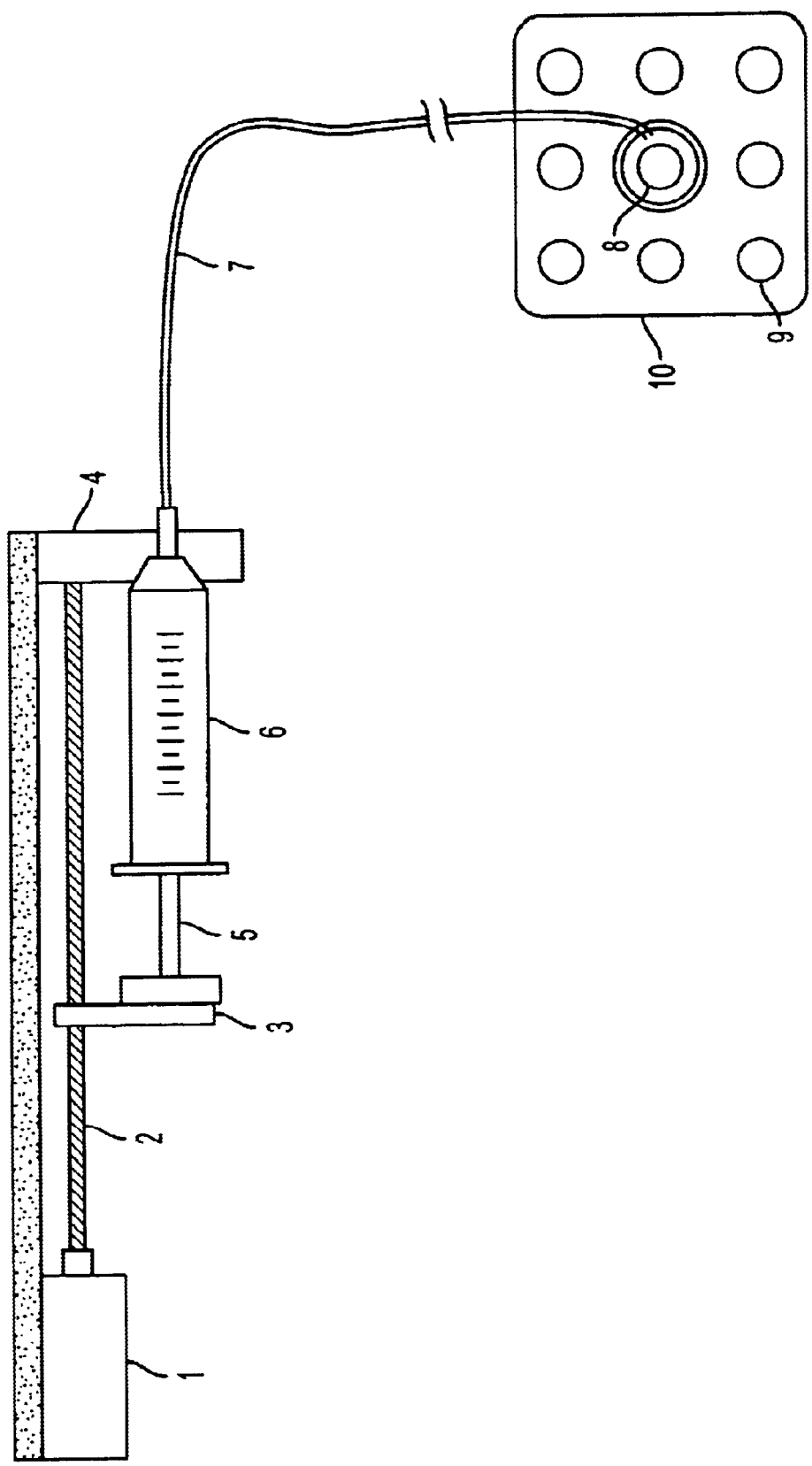
FIG. 12 shows a structure of an electroporation device according to a ninth embodiment of the invention.

In the ninth embodiment, the syringe 6 is preferably a disposable, single-use syringe, which is positioned adjacent to the probe (only the head 10 of the probe is shown in FIG. 12, whereby the rest of the probe is hidden behind the head 10 in the view provided in FIG. 12). The syringe 6 is inserted or fitted onto the frame 4, and does not move relative to the frame 4. For example, the frame 4 may be placed on a table next to a bed on which a patient to be treated is located.

The piston 5 is operable to move relative to the frame 4, whereby the movement is caused by the motor 1, the screw 2, and the slide 3, which operate together as a moving means. With the configuration shown in FIG. 12, the probe is free-standing and can be moved a certain amount (e.g., 1 to 10 feet, depending on the length of the tube 7) relative to the frame 4 (while maintaining a coupling to the syringe 6 by way of the tube 7 that couples the syringe 6 with the head 10 of the probe). That way, the probe can be moved around to treat different areas of a skin of a patient lying on a bed, while the frame containing the syringe 6 rests in place on a table next to the bed. In an alternative configuration, the probe and the syringe 6 can both be mounted on the frame 4, as a single-block construction. In this configuration, the entire frame is moved to different areas of the patient's skin, to thereby treat the patient by way of a probe that is inserted in the frame. The head of the probe extends out from one end of the frame, so that it can be placed against the patient's skin.

In a preferred implementation, the motor 1 is powered by a different power source than the source providing power to the probe. However, in a different implementation, the motor 1 and the probe may be powered by the same power source.

A tube or pipe 7 is used to connect the syringe 6 with the head 10 of the probe. The tube 7 is preferably a disposable, single-use component, and may be a flexible plastic tubing, for example. The head 10 is preferably a vibrating head, such as described earlier with respect to other embodiments. In an alternative configuration, the head 10 does not vibrate, and only electrical pulses are provided to the skin (so as to electroporate the skin to thereby absorb the substance provided to the skin by way of the syringe 6 and tube 7) in this alternative configuration. The tube 7 is preferably 0.5 to 3 millimeters in diameter, and is sized so as to allow a liquid or cream-like substance to flow through the tube 7, and exit the tube 7 at a second end opposite a first end of the tube 7 that is coupled to the syringe 6. Such a substance to be applied to the skin may include water-based collagen, water-based elastine, and anesthetic, or other type of drug, just to name a few.

Figure 14:
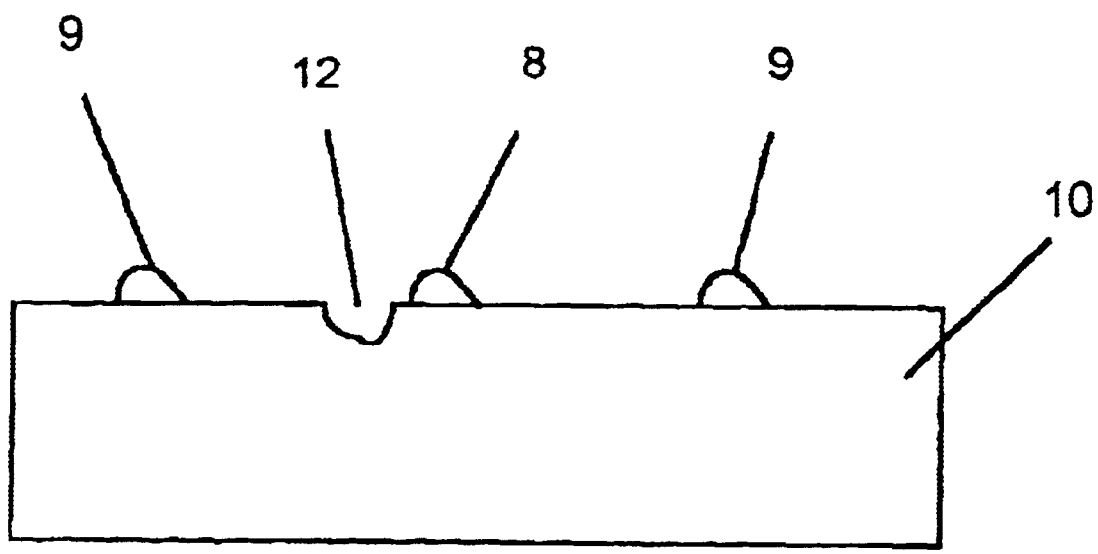
FIG. 14 shows a side view of the head of a probe used in an apparatus according to the ninth embodiment of the invention.

Referring now to FIG. 14, the tube 7 couples to the head 10 by way of a groove 12 that is located at an end of the head 10 and that is provided all the way to a groove 11 that surrounds the central electrode 8. The groove 12 is sized so as to accept the tube 7 fitted therein to provide a snug fit, whereby the tube 7 is preferably fitted within the groove 12 by feeding the tube 7 within the groove 12 from the end of the head 10 where one end of the groove 12 is disposed. In the ninth embodiment, the size of the groove 12 is such that the tube 7 does not extend above the upper surface of the head 10 (where the electrodes 8, 9 are disposed), or whereby the tube 7 extends slightly below the upper surface (plate) of the head 10. That way, the tube 7 will not be felt by the patient when the head 10 of the probe is moved along the skin of the patient during a treatment. Preferably, the tube 7 will not be in contact with the skin of the patient during treatment of the patient by way of a method and/or apparatus according to the ninth embodiment. The top surface of the head 10 preferably has a plate-like configuration, so as to provide a smooth feeling to the patient's skin.

On the top surface of the head 10 there are provided one central electrode 8 and a plurality of circumferential electrodes 9 disposed around the central electrode 8. The groove or trough 11 surrounding the central electrode 8 is preferably 1 mm wide, whereby the groove 11 is coupled to one end of the groove 12 in which a portion of the tube 7 is disposed. That way, when a substance is flowed out of the syringe 6 (by way of action by the motor 1, the screw 2 and the slide 3), the substance flows through the tube 7 (disposed within the groove 12) and thereby into the groove 11. The substance collects within the groove 11 surrounding the central electrode 8, and is absorbed by the skin during an electroporation treatment (using electrical pulses and mechanical vibrations) by way of the ninth embodiment. When the top surface (plate) of the head 10 is placed in contact with the patient's skin, the substance within the groove 11 comes into contact with the patient's skin, and is absorbed by the skin.

Although eight circumferential electrodes 9 are shown in FIG. 12, the invention according to the ninth embodiment can operate with different numbers of circumferential electrodes 9. For example, a minimum of two circumferential electrodes 9, disposed opposite from each other (with the central electrode 8 disposed therebetween), may be utilized in a different configuration. Also, four circumferential electrodes 9 and more than eight circumferential electrodes 9 may be utilized in other different configurations (e.g., 16 electrodes, 32 electrodes, or an odd number, such as three, five, or seven, circumferential electrodes surrounding the central electrode 8) of the ninth embodiment.

A pulse generator, such as the one shown in FIG. 4 (see also FIGS. 4A and 4B), is used to provide electrical pulses to the electrodes 8, 9 disposed on the head 10 of the probe. As explained earlier, the preferred shape of the electrical pulses is an exponential shape, as shown in FIG. 4B. Alternatively, sinusoidal or sawtooth waveforms may be provided, but exponential pulses provide a better skin transpiration effect. Operation of the pulse generator that may be utilized in the ninth embodiment has been described in detail with respect to the first embodiment described previously, and will not be described here for sake of brevity.

One of the two outputs of the pulse generator (see FIG. 4) is connected to the central electrode 8, and the other of the two outputs of the pulse generator is connected to one of the circumferential electrodes 9. The circumferential electrodes 9 are coupled to each other electrically on the back side of the head (see dashed line in FIG. 2C), so that each of the electrical pulses provided on the other of the two outputs of the pulse generator is provided to all of the circumferential electrodes 9 simultaneously.

The voltage of the electrical pulses provided to the skin from each of the eight circumferential electrodes 9 can be considered as a "ground" with respect to the voltage of the electrical pulse provided to the skin from the one central electrode 8. Since the central electrode 8 carries more electrical current than each of the eight circumferential electrodes 9, the circumferential electrodes 9 act like a ground connection, whereby the electrical current carried by each of the eight circumferential electrodes 9 is approximately eight times less than the electrical current carried by the central electrode 8.

The piston 5 of the syringe 6 is moved by the motor 1, which is a DC electric motor in a preferred implementation. The motor 1 is connected to the screw 2, which moves the piston 5 by way of the slide 3 that is attached to the screw 2 at a particular location on the screw 2. When the head 10 of the probe is positioned on a patient's skin, electrical pulses are delivered to the electrodes 8, 9, and the piston 5 of the syringe 6 is moved by the motor 1 in order to deliver the liquid or cream-like substance (or drug) from within the syringe 6 to the patient's skin. The liquid, cream or drug is preferably provided to the patient's skin in a slow, controlled manner, to allow the substance to be properly absorbed within the skin. For example, a water-based collagen, a water-based elastine, an anesthetic, or other type of drug may be provided within the syringe 6, to then be provided to the skin of a patient (to be absorbed therein) by way of the method and apparatus according to the ninth embodiment.

The enhancement of the skin absorption by electrical pulses applied to the skin, and also by mechanical vibrations applied to the skin at the same time in a synchronous manner (see description of the vibrating plate with respect to other embodiments) of the ninth embodiment, enables the absorption of a drug or other type of substance delivered by way of the syringe 6. A typical drug absorption quantity is 1 cubic centimeter in one to five minutes, by using the method and apparatus according to the ninth embodiment. In this regard, the timing of the movement of the piston 5 is such that the correct amount of substance is output from the syringe 6 during a treatment of a patient, whereby when the probe is turned on, this event will provide a trigger signal to the motor 1 to start to operate. Operation of the motor 1 will in turn cause the substance within the syringe 6 to be pushed out of the syringe 6, and into the groove 12 surrounding the central electrode 8.

The substance is introduced within the syringe at a previous time, so that the syringe 6 with the substance provided therein can then be attached to the frame 4, coupled to the tube 7, and thereby provide an apparatus that can introduce drugs and/or other substances to the skin of a patient, by way of a probe having a head 10 with electrodes 8, 9 provided on an outer surface or plate of the head 10. As explained earlier, the head 10 vibrates, so that both electrical and mechanical vibrations are provided to the patient's skin at a same time the drug or other substance is provided to the patient's skin (by way of the substance disposed within the trough or groove 12 being in contact with the patient's skin during a treatment of the patient). In an alternative configuration, which provides a skin transpiration effect not as good as using both mechanical vibrations and electrical pulses, only electrical pulses are provided to a patient's skin (the head does not vibrate). This configuration is cheaper to build, and may be suitable for certain instances.

The motor 1, screw 2, slide 3, piston 5, syringe 6, frame 4 and tube 7 may be coupled to different types of probes, in order to provide an apparatus for skin absorption enhancement and transdermal drug delivery. For example, any of the probes described with respect to the other embodiments (except those that have the substance stored in a container within the head of the probe) may be utilized with the components described above. Also, the structure for moving a substance out of the syringe 6 may be accomplished by ways other than the screw/slide/motor "moving means" described with respect to FIG. 12, while remaining within the scope of the invention.

Figure 13:
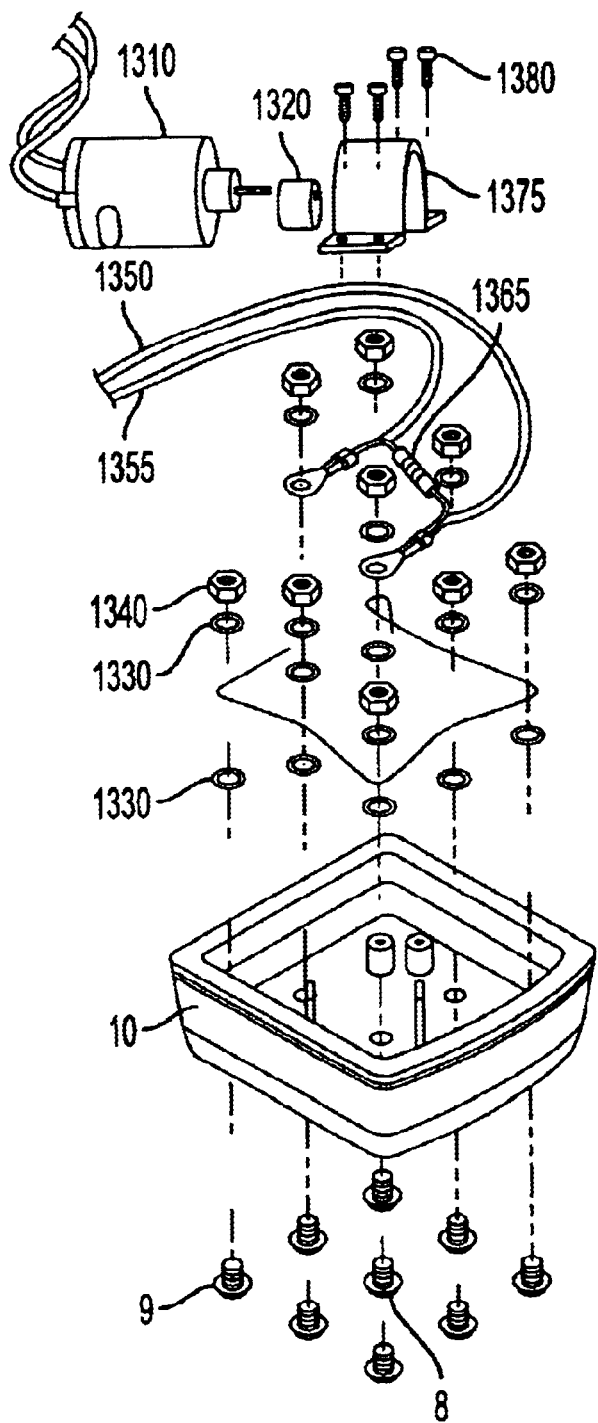
FIG. 13 shows components used to couple electrodes and wires to a head of the electroporation device according to the ninth embodiment of the invention.

FIG. 13 shows a back view of the head 10, whereby components used to couple the electrodes 8, 9 to the head and to provide an electrical connection to the electrodes 8, 9 are also shown in FIG. 13. A motor 1310, which includes an eccentric 1320 coupled to an output of the motor 1310, is used to provide mechanical vibrations to the head 10, so that the apparatus provides both electrical and mechanical vibrations to a patient's skin at the same time. These mechanical vibrations are preferable synchronized with the electrical pulses, as described earlier with respect to other-described embodiments of the invention.

The electrodes 8, 9 are preferably screwed onto the front plate of the head 10. Washers 1330 and screws 1340 are utilized to electrically couple wires 1350, 1355 to the electrodes 8, 9. In particular, wire 1350 (that has one end coupled to one of the two outputs of the pulse generator as shown in FIG. 4, for example) is electrically connected to the central electrode 9, and wire 1355 (that has one end coupled to the other of the two outputs of the pulse generator as shown in FIG. 4, for example) is electrically connected to the circumferential electrodes 8. Resistor 1365 is provided between the wires 1350, 1355, in the preferred construction. Also shown in FIG. 13 is a housing 1375 which is coupled to the head 10 by way of screws 1380. The eccentric 1320 moves within the housing 1375, thereby causing vibrations that are translated to the head 10 of the probe.

Figure 15:
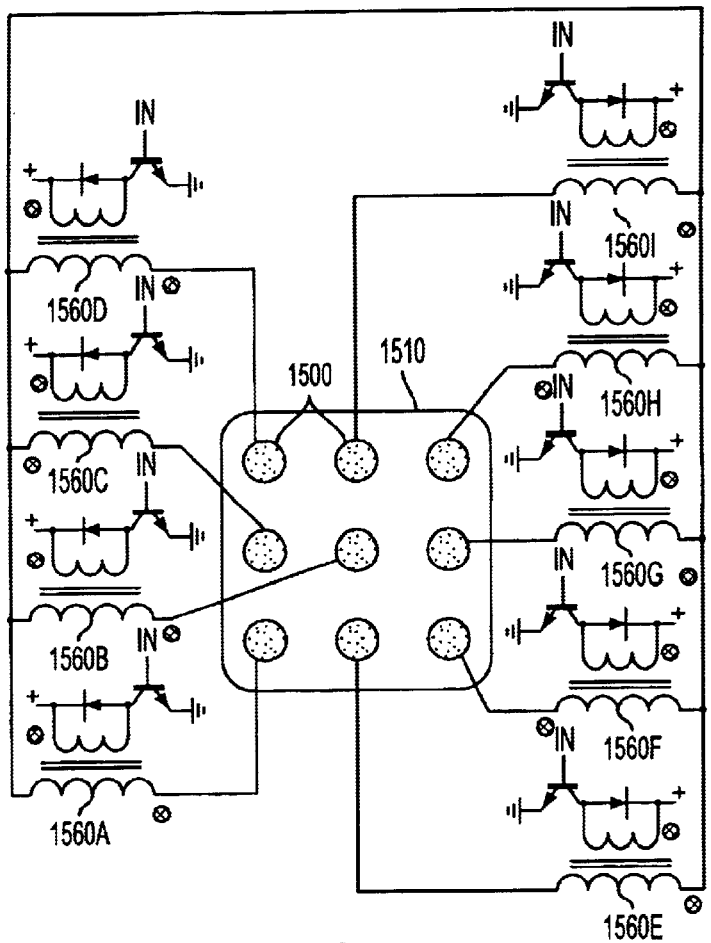
FIG. 15 shows a back view of the head of a probe, along with transformers shown, in an apparatus according to a tenth embodiment of the invention.
Figure 16:
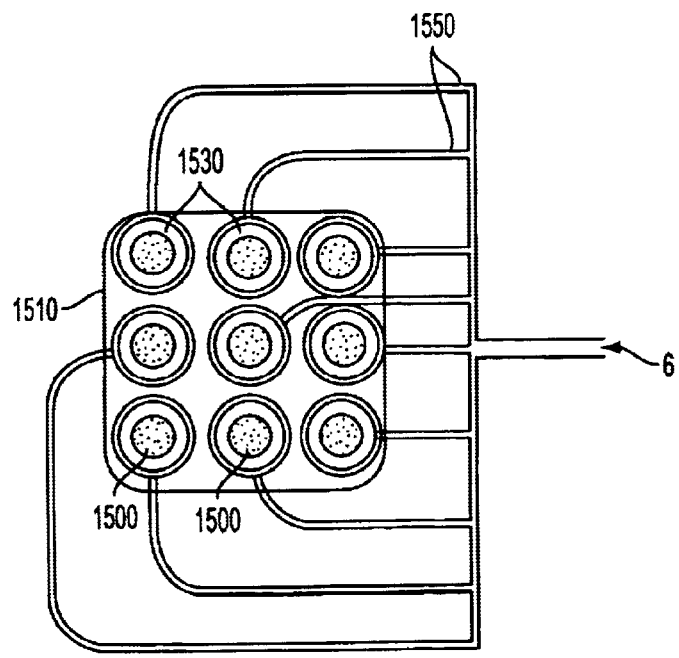
FIG. 16 shows a front view of the head of a probe used in an apparatus according to the tenth embodiment of the invention.

A tenth embodiment of the invention will be described herein with respect to FIGS. 15 and 16. The tenth embodiment is similar to the ninth embodiment, but utilizes a different configuration for the head, as well as providing a plurality of transformers (see FIGS. 4, 4A and 4B). FIG. 15 shows a back view of the electrodes 1500 disposed on a head 1510 of a probe, and FIG. 16 shows a front (skin-side) view of the electrodes 1500, whereby each electrode has a groove or trough 1530 surrounding it. Each groove 1530 has an outlet that extends to an edge of the head 1510, to thereby allow a respective tube 1550 to be fitted therein, so as to provide an amount of substance from the syringe 6 to the grooves 1530. That way, the tubes 1550 do not extend above the top surface of the head 1510. As an alternative to the multi-port tube configuration shown in FIG. 16, a number of syringes equal in number to the number of electrodes may be provided, with a tube provided to couple a syringe to an electrode.

In the tenth embodiment, each electrode 1500 is active and is connected to its own pulse transformer 1560A–1560I. The substance from the syringe 6 is provided to grooves 1530 surrounding each of the electrodes 1500. The electronic pulses are provided to each of the electrodes 1530 from the respective pulse transformers 1560A–1560I, whereby transformers 1560C, 1560E, 1560G and 1560I provide positive pulses to their respective electrodes, and whereby transformers 1560A, 1560B, 1560D, 1560F and 1560H provide negative pulses to their respective electrodes at the same time, for the nine electrode configuration. More particularly, transformers 1560C, 1560E, 1560G and 1560I have their primary and secondary windings connected in phase, and transformers 1560A, 1560B, 1560D, 1560F and 1560H have their primary and secondary windings connected 180 degrees out of phase (see oppositely-positioned dots for those transformers in FIG. 15). If a square wave is applied to all of the primary windings of the transformers at the same time and when there is a positive transition from low to high, the transformers with their primary and secondary windings in phase with each other will output a positive exponential pulse, and the transformers with their primary and secondary windings 180 degrees out of phase with each other will output a negative exponential pulse.

In the tenth embodiment, it is preferable that a first group of electrodes receive a positive pulse at a same time a second group of electrodes (equal or nearly equal in number to the first group, preferably) receive a negative pulse, to provide a good skin transpiration effect. The type of pulses, the burst duration, the frequency, etc., are similar to the embodiments described earlier. Also, the tenth embodiment may include a mechanical vibration that is applied to the patient's skin at the same time the electrical pulses are applied to the patient's skin, in a manner described previously.

In an eleventh embodiment, a plurality of transformers are respectively provided to output electrical pulses to a plurality of electrodes disposed on a head portion of a probe, whereby the plurality of transformers provide separate and independent pulse bursts to their respective electrodes. For example, each of the pulse generators in the eleventh embodiment may have different phase shift amounts within a range of from 0 degrees to 360 degrees. In this regard, the output pulses from the transformers are synchronized with each other, to have a particular out-of-phase relationship with respect to each other.

Figure 17:
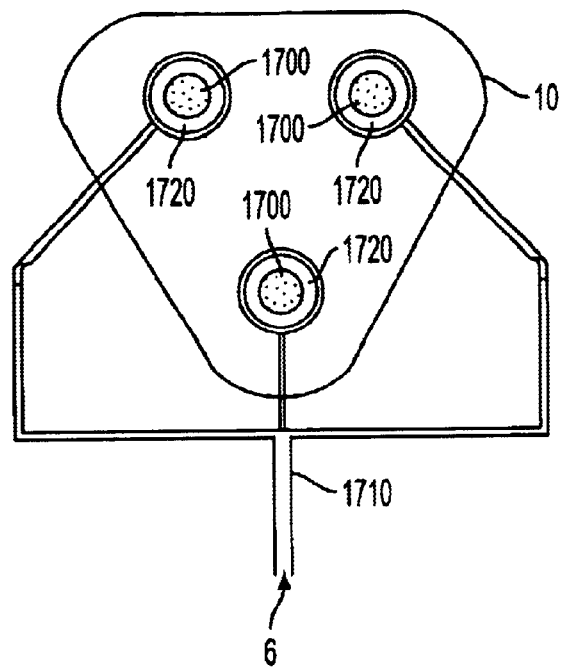
FIG. 17 shows a front view of the head of a probe having three electrodes, which is used in an apparatus according to an eleventh embodiment of the invention.
Figure 18:
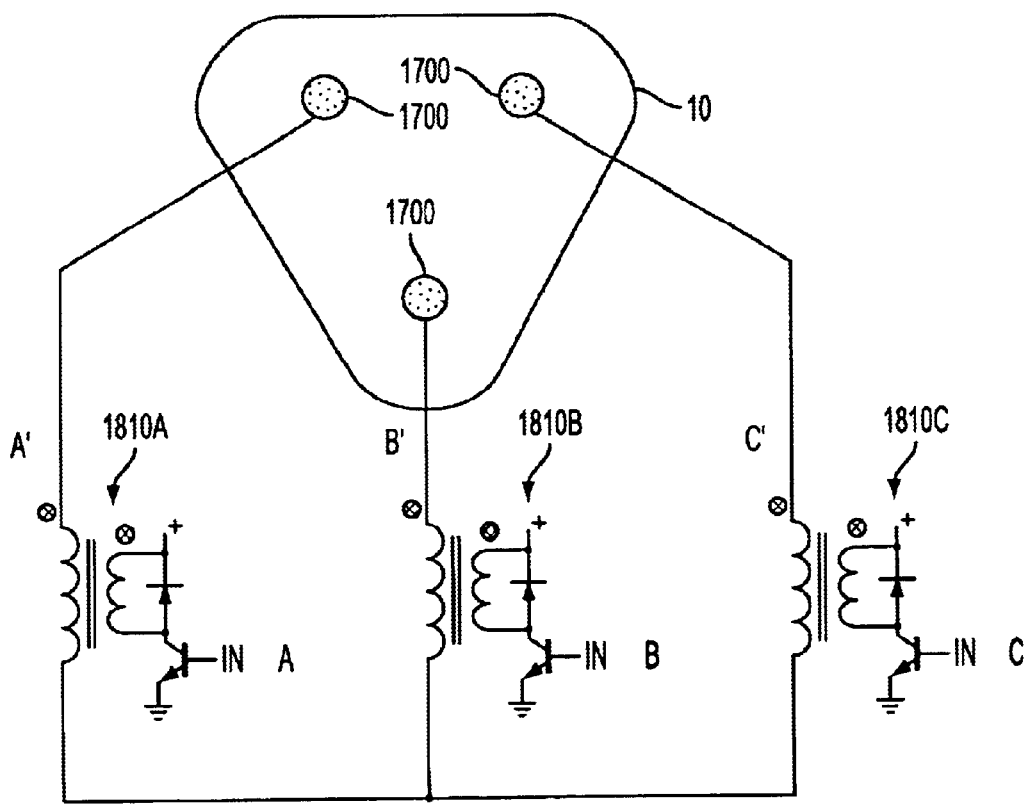
FIG. 18 shows a back view of the head of a probe having three electrodes, along with transformers providing electronic pulses to the three electrodes, which is used in an apparatus according to the eleventh embodiment of the invention.
Figure 19:
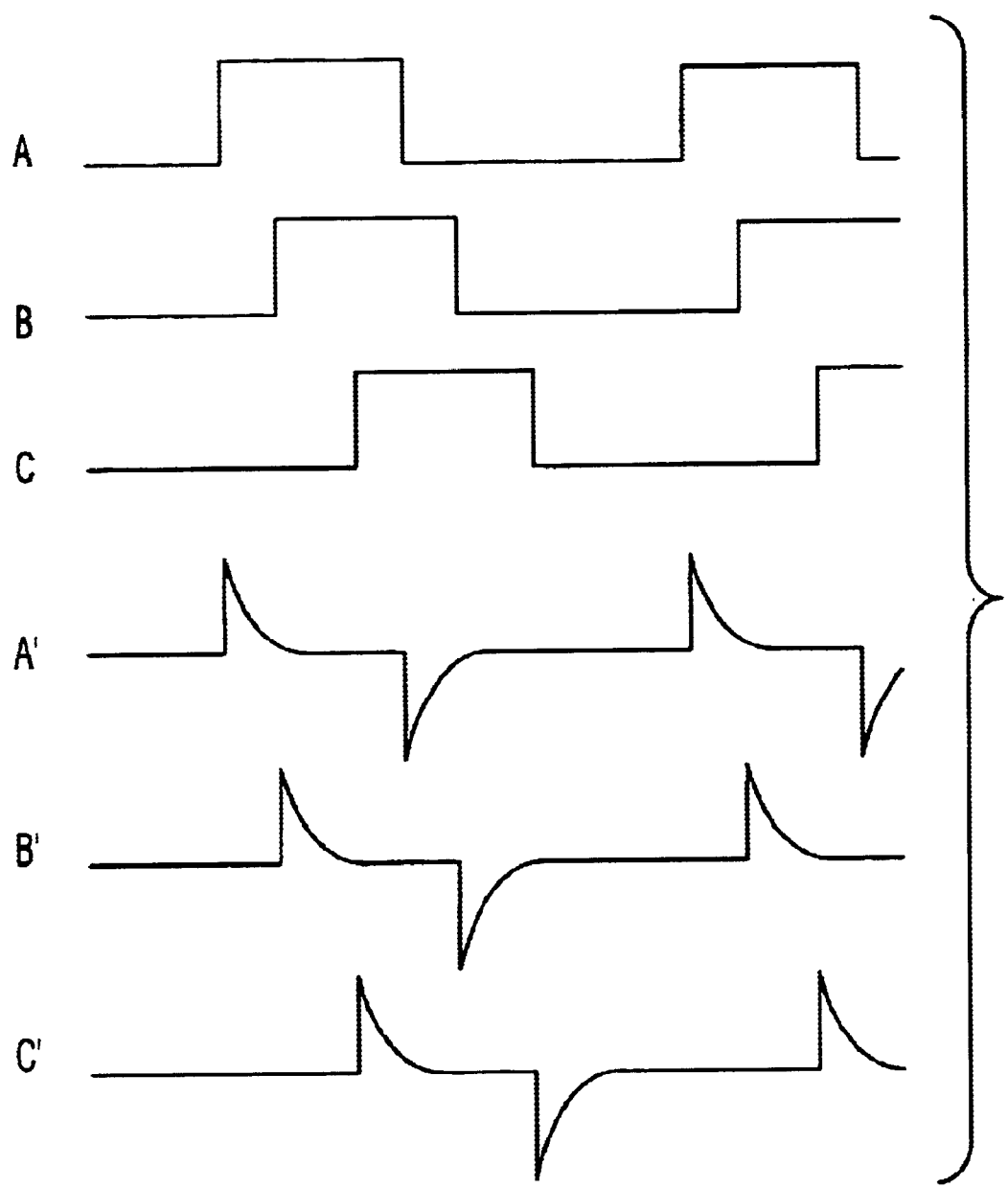
FIG. 19 shows staggered square-wave input pulses and exponential outputs pulses with respect to the three transformers which is used in an apparatus according to the eleventh embodiment of the invention.

One example of an electrode array according to the eleventh embodiment is shown in FIGS. 17, 18 and 19. This example provides a three electrode configuration, with no central electrode. Referring now to FIG. 17, which shows a front side of the head 10, electrodes 1700 are respectively coupled via tube 1710 to a syringe 6, to receive a substance in a groove 1720 surrounding each of the electrodes 1700. Like the previously-described embodiments, as shown in FIG. 14, a groove or path to an end of the head 10 is provided, in order to fit the tube 1710 snugly within it so that the tube 1710 does not extend above the upper surface (plate) of the head 10 that makes contact with a patient's skin.

Referring now to FIG. 18, which shows a back side of the head 10, transformers 1810A, 1810B and 1810C respective provide pulses of the same polarity, but delayed from each other by a particular amount, to the corresponding one of the electrodes 1700 coupled to each transformer. FIG. 19 shows the input square wave pulses that are provided to each transformer, whereby the square wave pulses that are input to transformer 1810C are delayed a certain amount (e.g., 30 degrees) with respect to the square pulses that are input to transformer 1810B, which in turn are delayed a certain amount (e.g., 30 degrees) with respect to the square wave pulses that are input to transformer 1810A. This can readily be done by providing the trigger "IN" signal to each of the respective transformers 1810A, 1810B, 1810C at the appropriate timings. The result are exponential pulses that are output from each of the three pulse generators, whereby the exponential pulses are phase-shifted a fixed amount with respect to each other.

With the three-electrode and three-pulse-generator configuration as shown in FIGS. 17–19, it is possible to provide a 120 degree phase shift with respect to the signals output by the three pulse generators (e.g., one signal output at 0 degrees, one signal output at 120 degrees, and one signal output at 240 degrees). This provides a rotation of the electric field between the electrodes 1700 in a manner similar to what happens with a rotation of a three-phase motor. More generally, in the eleventh embodiment, using a number "n" of electrodes and "n" pulse generators, one of ordinary skill in the art will understand that one can devise any particular type of electric field distribution on the skin surface to be treated by way of an apparatus according to the eleventh embodiment, as desired.

Experimental results of the application of the several embodiments of the skin absorption apparatus described hereinabove to the skin demonstrated that a noticeable variation of results and rate of absorption of substances occurred. The analysis was carried out over an area of skin previously dermabraded with a standard microdermabrader available on the market and an adjacent area not previously dermabraded. This analysis demonstrated that the results obtained in the dermabraded area are fairly constant and reproducible while the results in the non-dermabraded area are variable and somewhat inconsistent. This inconsistency is due to the fact that the stratum corneum (also referred to as the horny or dead outermost layer of the epidermis) of the skin acts like a barrier to the absorption of the substances applied to the skin, and moreover it increases the electrical resistance of the skin, thereby somewhat decreasing the absorption effect of the skin absorption treatment according to the invention.

The thickness of the stratum corneum is variable from person to person, and moreover it is variable from time to time in the same person. This induces a variability that makes it difficult to come up with a standard application time of the skin absorption apparatus according to the various embodiments of the invention. For this reason, according to yet another embodiment of the invention, a skin absorption treatment method includes a microdermabrasion performed before the application of the skin absorption apparatus in order to give more reproducible and more constant results as compared to the embodiments in which a microdermabrasion is not first performed. The microdermabrasion to be performed prior to the skin absorption treatment may be one described in various U.S. patents assigned to Mattioli Engineering, Ltd., such as U.S. Pat. Nos. 6,322,568 and 6,039,745, each of which are incorporated in their entirety herein by reference, or other types of dermabrasion treatments conventionally known.

Preferably, the dermabrasion treatment is performed for three minutes in order to remove a 100 micron layer of the corneum status of the skin in an area to be later treated with a skin absorption enhancement device according to one of the embodiments of the invention. Ideally, the skin absorption treatment is performed soon after (e.g., within 5 minutes) of the completion of the dermabrasion treatment. Of course, other time lengths of dermabrasion treatment, depth of corneum status removal, and time between the dermabrasion treatment and the skin absorption treatment, may be contemplated while remaining within the scope of the invention as described hereinabove.

Different embodiments of the present invention have been described according to the present invention. Many modifications and variations may be made to the techniques and structures described and illustrated herein without departing from the spirit and scope of the invention. Accordingly, it should be understood that the apparatuses described herein are illustrative only and are not limiting upon the scope of the invention.

What is claimed is:

1. A treatment method for enhancing absorption of substances provided on a skin surface of a patient, comprising:
    a) applying a substance within a syringe;
    b) applying a sequence of bursts of electrical pulses to an array of electrodes that are placed a region of the skin, the array of electrodes being disposed on a head of a probe; and
    c) at the same time as step b), causing the substance to be output from the syringe and onto the head of the probe, in a controlled manner,
    wherein the sequence of bursts of electrical pulses are provided to the region of the skin in order to enhance absorption of the substance applied to the region of the skin,
    wherein the electrodes are round electrodes with one central electrode and a plurality of non-central electrodes disposed around the central electrode,
    wherein one electrical pulse is provided solely to the one central electrode, and
    wherein another electrical pulse is provided to the plurality of non-central electrodes that are electrically connected to each other but not to the one central electrode.

2. The treatment method according to claim 1, further comprising:
    d) at a same time as step b) and step c), applying a mechanical vibration to the region of the skin of between 10 to 200 Hz, the mechanical vibration being provided by vibrating the head of the probe.

3. The treatment method according to claim 1, wherein a D.C. current is applied between the electrodes and a ground plate connected to the patient.

4. The treatment method according to claim 1, wherein the sequence of pulses are provided at a frequency between 50 to 15,000 Hz and peak voltage between 20 and 200 V.

5. The treatment method according to claim 1, further comprising:

prior to step a), performing a dermabrasion on the region of the skin.

6. An apparatus for enhancing absorption of substances provided on a skin region of a patient, comprising:

an array of electrodes provided on a head of a probe;

a syringe that is configured to hold the substance to be provided on the skin region of the patient;

a frame in which the syringe is fixedly mounted;

a pulse generator configured to generate a sequence of bursts of electrical pulses to the array of electrodes that are placed on the skin; and moving means for moving a piston of the syringe so as to output a particular amount of the substance from the syringe and onto the head of the probe at a particular rate, wherein the sequence of bursts of electrical pulses are provided to the skin region by way of the array of electrodes at the same time the outputting means is causing the substance to be output from the syringe, in order to enhance absorption of the substance applied to the skin region when the head of the probe is placed against the skin region of the patient, wherein the array of electrodes comprises:

a central electrode; and a plurality of non-central electrodes disposed around the central electrode, wherein a groove is provided only around the central electrode and not around said plurality of non-central electrodes in order to accept the substance output from the syringe.

7. The apparatus according to claim 6, wherein the electrical pulses are output at a frequency between 50 to 15,000 Hz and peak voltage between 20 and 200 V.

8. The apparatus according to claim 6, wherein the moving means comprises:

a motor;

an output rod coupled to the motor and configured to rotate when the motor operates; and a slide coupled to one end of the output rod, wherein the slide is disposed against the piston of the syringe, and operates to push the piston inwards when the motor operates.

9. The apparatus according to claim 6, further comprising:

a tube that couples the syringe to the groove wherein the tube is adapted to fit within a trough provided on the head of the probe to thereby have an end of the tube provided adjacent to the groove, wherein the substance flows from the syringe and into the groove by way of the tube.

10. The apparatus according to claim 6, further comprising:

a motor; and an eccentric for receiving output from the motor and for providing an eccentric force to the head of the probe, the eccentric force causing mechanical vibrations of the head which are translated to the skin of the patient when the head of the probe is in contact with the skin of the patient.

11. The apparatus according to claim 10, further comprising:

a controller for synchronizing the mechanical vibrations with the electrical pulses such that a vibration frequency of the mechanical vibrations is frequency-synchronous with a burst frequency of the sequence of bursts of electrical pulses.

12. An apparatus for enhancing absorption of substances provided on a skin region of a patient, comprising:

an array of electrodes provided on a head of a probe;

a syringe that is configured to hold the substance to be provided on the skin region of the patient;

a frame in which the syringe is fixedly mounted;

a pulse generator configured to generate a sequence of bursts of electrical pulses to the array of electrodes that are placed on the skin;

moving means for moving a piston of the syringe so as to output a particular amount of the substance from the syringe and onto the head of the probe at a particular rate;

a plurality of electrodes disposed a particular distance from each other;

a plurality of grooves respectively provided on a one-to-one basis around the plurality of electrodes; and a plurality of tubes respectively provided on a one-to-one basis for said plurality of electrodes and configured to provide the substance to said plurality of grooves for application to the skin region of the patient, wherein said plurality of tubes are connected at one end to said syringe and at an opposite end to a respective one of said plurality of electrodes, and wherein the sequence of bursts of electrical pulses are provided to the skin region by way of the array of electrodes at the same time the outputting means is causing the substance to be output from the syringe, in order to enhance absorption of the substance applied to the skin region when the head of the probe is placed against the skin region of the patient.

13. An apparatus for enhancing absorption of substances provided on a skin region of a patient, comprising:

an array of electrodes provided on a head of a probe;

a syringe that is configured to hold the substance to be provided on the skin region of the patient;

a pulse generator configured to generate a sequence of bursts of electrical pulses to the array of electrodes that are placed on the skin;

a vibrating unit configured to provide mechanical vibrations to the head of the probe; and a pipe that is configured to provide the substance from the syringe to the head of the probe, wherein the sequence of bursts of electrical pulses and the mechanical vibrations are provided to the skin region at the same time the substance is provided to the head of the probe in a frequency synchronous manner such that a frequency of application of the bursts of electrical pulses is a same as a frequency of application of the mechanical vibrations, in order to enhance absorption of the substance applied to the skin region when the head of the probe is placed against the skin region of the patient.

14. The apparatus according to claim 13, wherein the array of electrodes comprises:

a plurality of electrodes disposed a particular distance from each other, wherein a groove is provided around at least one of the electrodes in order to accept the substance output from the syringe.

* * * * *